United States Patent
Yamashita et al.

(10) Patent No.: US 6,328,979 B1
(45) Date of Patent: Dec. 11, 2001

(54) SUSTAINED RELEASE MEDICINAL COMPOSITIONS

(75) Inventors: Noboru Yamashita; Akira Takagi; Masataka Katsuma; Katsumi Saito; Yuuki Takaishi; Tatsuo Yasuda; Yutaka Takahashi; Mitsuo Mitomi, all of Shizuoka Ken (JP)

(73) Assignee: Yamanouchi Pharmaceuticals, Co. Ltd., Tokyo (JP)

( * ) Notice: Subject to any disclaimer, the term of this patent is extended or adjusted under 35 U.S.C. 154(b) by 0 days.

(21) Appl. No.: 09/582,384

(22) PCT Filed: Dec. 25, 1998

(86) PCT No.: PCT/JP98/05916

§ 371 Date: Jun. 23, 2000

§ 102(e) Date: Jun. 23, 2000

(87) PCT Pub. No.: WO99/33491

PCT Pub. Date: Jul. 8, 1999

(30) Foreign Application Priority Data

Dec. 26, 1997 (JP) .................................................... 9-360265

(51) Int. Cl.⁷ ................................ A61K 9/00; A61K 9/52; A61K 9/22; A61F 2/00
(52) U.S. Cl. ........................ 424/400; 424/457; 424/468; 424/423
(58) Field of Search ................................ 424/451, 489, 424/454, 480, 50, 486, 502, 487, 488, 400, 468, 457, 426, 423, DIG. 15; 514/937

(56) References Cited

U.S. PATENT DOCUMENTS

| | | | | |
|---|---|---|---|---|
| 5,575,987 | * | 11/1996 | Kamel et al. | 424/451 |
| 5,741,524 | * | 4/1998 | Staniforth et al. | 424/489 |

FOREIGN PATENT DOCUMENTS

| | | |
|---|---|---|
| 2-300109 | 2/1990 | (JP) . |
| 4-41432 | 2/1992 | (JP) . |
| 5-238959 | 9/1993 | (JP) . |

* cited by examiner

Primary Examiner—Thurman K. Page
Assistant Examiner—Blessing Fubara
(74) Attorney, Agent, or Firm—Townsend and Townsend and Crew LLP

(57) ABSTRACT

The present invention relates to sustained-release pharmaceutical compositions for ionic pharmaceutically active substances (excluding ionic prostanoic acid derivatives) containing ionic compounds having opposite charges to those of the active substances and increasing hydrophobicity of the active substances. More specifically, the invention relates to sustained-release pharmaceutical compositions comprising the ionic pharmaceutically active substances and the ionic compounds having opposite charges to those of the active substances and increasing hydrophobicity of the active substances that contain hydrophobic groups in the molecule thereof. The pharmaceutical composition of the invention can exhibit excellent sustained release effect of the active substance, irrespective of water solubility possessed by the ionic pharmaceutically active substances.

12 Claims, 2 Drawing Sheets

SUSTAINED RELEASE MEDICINAL COMPOSITIONS

FIELD OF THE INVENTION

The present invention relates to a sustained-release pharmaceutical composition for an ionic pharmaceutically active substance (excluding an ionic prostanoic acid derivative). More particularly, the invention relates to a sustained-release pharmaceutical composition comprising an ionic pharmaceutically active substance and an ionic compound which has an opposite charge to that of the ionic pharmaceutically active substance and enhances the hydrophobic property of the ionic pharmaceutically active substance.

RELATED ART

Oral administration has been widely applied to delivery of pharmaceutically active substances. While there is a need for fast-acting drugs, both fast and continuously acting drugs are simultaneously necessary sometimes. In this case, parenteral administration is generally used in combination with oral administration. For parenteral preparations, there are known intravenous, subcutaneous or intramuscular injection; implants and transmucosal preparations through oral cavity, nasal cavity, lung, vagina, rectum, skin, etc. Of these routes, injection is a general choice for administration.

However, sustained release of some medicaments may cause difficulty in parenteral preparations, depending upon the property of a pharmaceutically active substance. For example, such difficulty is noted with pharmaceutically active substances having a short half life in blood, a high water solubility or a low molecular weight. When it is desired to maintain the pharmacological effects of those medicaments over a long period of time, it is the actual practice to administer such a medicament by instillation through the vein or frequently inject the medicament subcutaneously or intramuscularly. A burden of such a treatment is not negligible to patients either physically or mentally. To solve the problem, it has been investigated to create a pharmaceutically active substance having a prolonged half life in blood or to produce a hybrid between a pharmaceutically active substance and a high molecular weight substance such as polyethylene glycol by irreversible bonding of the two substances, thereby to extend the half life of the pharmaceutically active substance itself in blood. Various other techniques for controlling the solubility or dissolution of a pharmaceutically active substance out of a carrier have been studied, which involve insolubilizing or sparingly solubilizing a pharmaceutically active substance in water to delay its dissolution, or microencapsulation of a pharmaceutically active substance using a biodegradable high molecular weight material.

For example, Japanese Patent Application Laid-Open No. 1-163199 discloses that an organic acid with a high molecular weight of about 5,000 or more, e.g., sodium alginate, is added to a cytokine like interleukin 2 so as to reach the isotonic osmotic pressure or more and the mixture is then shaken to form the water-insoluble matter, whereby the insoluble mater is used in a sustained-release composition for injection.

Japanese Patent Application Laid-Open No. 9-208485 discloses a sustained-release preparation comprising a sparingly water-soluble composition formed from a peptide-proteinaceous medicament and EDTA.

Japanese Patent Application Laid-Open Nos. 8-3055 and 8-217691 disclose sustained-release preparations comprising microcapsules obtained by mixing a water-soluble pharmaceutically active substance and a water-soluble polyvalent metal salt, and dispersing the resulting water-insoluble mixture of in a biodegradable high molecular weight material such as polylactic acid-glycolic acid copolymer.

On the other hand, Japanese Patent Application Laid-Open No. 62-129226 discloses that hyaluronic acid or its sodium salt, or Hylan enables a medicament dissolved or dispersed in the solution to achieve continuous release from the solution mainly based on the viscosity of the solution. This publication also discloses that in a cationic group-containing medicament, exchange of ions could occur between this carboxyl group-containing macromolecule of hyaluronic acid and the medicament, where the exchange causes slower diffusion of the medicament out of the system. As a technique utilizing the viscosity of hyaluronic acid, Japanese Patent Application Laid-Open No. 1-287041 discloses a sustained-release preparation suitable for subcutaneous or intramuscular administration, comprising a pharmaceutically active substance and hyaluronic acid or a salt thereof; Japanese Patent Application Laid-Open No. 2-213 also discloses a sustained-release preparation comprising a physiologically active peptide and hyaluronic acid or a salt thereof However, such a sustained-release preparation utilizing the viscosity of hyaluronic acid provides a fast diffusion of a pharmaceutically active substance from the viscous product, in which the active substance is incorporated. Even taking into account the ionic interaction ability between hyaluronic acid and a cationic medicament coupled to the viscosity of hyaluronic acid, it is suspected that retardation in dissolution is not enough. Yet, any sustained-release parenteral preparation that is satisfactory from a clinical standpoint has been unknown for not only cationic but also ionic pharmaceutically active substances. Particularly in the case of a highly water-soluble ionic pharmaceutically active substance, sustained release could not be attained to a satisfactory extent by the prior art technique of retarding the diffusion using the viscosity of a high molecular weight substance, especially because of its high water solubility.

Japanese Patent Application Laid-Open No. 53-18723 discloses a composition for rectal administration obtained by intimately mixing insulin with a quaternary ammonium salt cationic surfactant. Japanese Patent Application Laid-Open No. 59-89619 discloses a liquid pharmaceutical composition for nasal administration, comprising calcitonin and benzalkonium chloride in a liquid diluent or carrier suitable for application to nasal mucous membrane. However, the techniques described in these gazette publications all aim at improving absorption of a medicament by rectal administration or nasal administration but none of the publications mentions or even suggests sustained release of a medicament involving the imparted hydrophobic property of an ionic complex.

DISCLOSURE OF THE INVENTION

An object of the present invention is to provide a sustained-release preparation of an ionic pharmaceutically active substance, irrespective of water solubility of the active substance, to such an extent that is satisfactory for clinical use.

Under the foregoing technical level, the present inventors attempted to provide a sustained-release preparation for an anionic pharmaceutically active substance, for which sustained release is required through parenteral route, first by adding an equimolar amount of a cationic compound to the anionic pharmaceutically active substance and forming a sparingly water-soluble ionic complex through ionic interaction between the anionic and cationic compounds, with an expectation to achieve a sustained release. However, subcutaneous administration of the ionic complex formed to rats revealed that no satisfactory sustained-release was obtained. It was thus found that the retarded dissolution of anionic pharmaceutically active substances is insufficient for the purpose of sustained release of ionic pharmaceutically active substances by parenteral route.

In order to further increase the hydrophobicity of the pharmaceutically active substance accompanied by the formation of the ionic complex, the present inventors have brought attention to an octanol/water partition coefficient as an index for the hydrophobicity. As a result, it has been found that depending upon kind of the cationic compound, there is a difference in the partition coefficient of the cationic pharmaceutically active substance associated with the ionic complex formation and that a better sustained release effect is obtained with a larger partition coefficient. It has also been found that the sustained release effect can be more enhanced by increasing the addition amount of the cationic compound and increasing the partition coefficient for the anionic pharmaceutically active substance. Furthermore, it has been discovered that these ionic complexes unexpectedly exhibit an excellent sustained release effect, even when a dissolved state of the pharmaceutically active substance in water is maintained, that is, the state of its aqueous solution is maintained if the pharmaceutically active substance is water-soluble.

The present inventors have confirmed that a sustained release of the ionic pharmaceutically active substance attained by increasing the hydrophobic level of a pharmaceutically active substance is effective for not only an anionic pharmaceutically active substance but also a variety of cationic medicaments. It was hitherto unknown that a sustained release can be attained by the increased hydrophobic level of ionic pharmaceutically active substances. Based on the finding that such a technique is advantageously applicable not only to parenteral preparations but to oral preparations, the present invention has been found.

(1) That is, the present invention relates to a sustained-release pharmaceutical composition comprising an ionic pharmaceutically active substance (excluding an ionic prostanoic acid derivative) and an ionic compound having an opposite charge to that of the ionic pharmaceutically active substance and increasing hydrophobicity of the active substance.

(2) The present invention also relates to a sustained-release pharmaceutical composition according to (1), wherein the ionic compound having an opposite charge to that of the ionic pharmaceutically active substance and increasing the hydrophobic property of the active substance contains a hydrophobic group in the molecule thereof.

(3) The present invention also relates to a sustained-release pharmaceutical composition according to (1) or (2), wherein the ionic compound increases an oil/water partition coefficient of the ionic pharmaceutically active substance.

(4) The present invention further relates to a sustained-release pharmaceutical composition according to any one of (1) to (3), wherein the ionic compound is incorporated at least in an equimolar amount based on the pharmaceutically active substance in terms of a charge ratio.

The sustained-release pharmaceutical composition of the present invention is characterized in that by adding a particular counter ion to the ionic pharmaceutically active substance to increase the oil/water partition coefficient of the ionic pharmaceutically active substance, a hydrophobic property is imparted to give the sustained-release pharmaceutical composition of the invention suitable for, e.g., injection. The sustained release according to the present invention is effected by means of a novel method quite different from conventional techniques adopted to control the release of ionic pharmaceutically active substances, to insolubilize a pharmaceutically active substance itself, to retard the dissolution of the active substance by microencapsulation, etc.. Moreover, the present invention is characterized in that the sustained release can be achieved in the present invention to a fully satisfactory extent that was obtained only insufficiently by these known means.

The sustained-release pharmaceutical composition of the present invention will be described below in more detail.

The ionic pharmaceutically active substance used in the present invention is not particularly limited, so long as the substance is provided generally pharmacologically for a treatment and its sustained release is desired for oral or parenteral administration. Examples of the anionic pharmaceutically active substance include antipyreteic and antiinflammatory agents such as fulfenamic acid, mefenamic acid, salicylic acid, indomethacin, alclofenac, diclofenac, alminoprofen, ibuprofen, etodolac, oxaprozin, ketoprofen, diflunisal, sulindac, tiaprofen, tolmetin, naproxen, calcium fenoprofen, pranoprofen, flurbiprofen, sodium roxoprofen, lobenzarit disodium, etc.; hypnotic tranquilizers such as sodium amobarbital, etc.; local anesthetics such as hopantenic acid, etc.; muscle relaxants such as dantrolene, etc., antispasmodic agents such as baclofen, etc.; antidiuretic agents such as furosemide, etacrynic acid, piretanide, etc.; antihypertensive agents such as captopril, enalapril, methyldopa, etc.; antihyperlipemic agents such as pravastatin, hormones such as liothyronine, levothyroxine, betamethasone phosphate, prednisolone succinate, etc.; bone metabolism improving agents such as minodronic acid, etc.; hemostatic agents such as carbazochrome sulfate, thrombin, tranexamic acid, etc.; medicaments for the treatment of gout such as probenecid, etc., metabolism-associated agents such as chondroitin sulfate, adenosine triphosphoate, etc.; antiallergic agents such as cromoglicic acid, tranilast, etc.; antibiotics such as ampicillin, cefaclor, cefalexin, cefpiramid, cefotetan, etc.; anti-tuberculosis agents such as p-aminosalicylic acid, etc.; medicaments for blood and body fluids; medicaments for the treatment of liver disorders such as glucuronic acid, etc.; vitamins such as biotin, calcium pantothenate, etc. These anionic pharmaceutically active substances may be in the form of pharmaceutically acceptable salts thereof or free acids thereof.

The anionic pharmaceutically active substances may also be associated with expression of peptides, for example, nucleic acids such as DNA, RNA, etc., transcription regulators of a high or low molecular weight and inhibitors thereof.

The cationic pharmaceutically active substances include anti-parkinsonism agents such as amantadine hydrochloride, biperidene hydrochloride, etc.; psychotropic agents such as chlorpromazine hydrochloride, perphenazine, perphenazine maleate, imipramine hydrochloride, amitriptyline hydrochloride, etc.; local anesthetics such as procaine hydrochloride, lidocaine hydrochloride, dibucaine hydrochloride, etc.; muscle relaxants such as suxamethonium chloride, etc.; agents for the autonomic nervous system such as acetylcholine chloride, methylbenactyzium bromide, distigmine bromide, torazoline hydrochloride, etc.; antispasmodic agents such as scopolamine hydrobromide, atropine sulfate, etc., agents for the treatment of arrhythmia such as procainamide hydrochloride, etc.; circulatory agents such as hydralazine hydrochloride, bencyclan fumarate, etc.; antihypertensive agents such as amosulalol hydrochloride, nicardipine hydrochloride, betanidine sulfate, etc.; vasodilating agents such as diltiazem hydrochloride, etc.; antitussive agents such as ephedrine hydrochloride, dl-methylephedrine hydrochloride, etc.; agents for the treatment of peptic ulcer such as famotidine, etc.; urogenital agents such as tamsulosin hydrochloride, etc.; anti-vomiting agents such as ramosetron hydrochloride, etc.; agents for blood and body fluids such as ticlopidine hydrochloride, etc.; alkylating agents such as cyclophosphamide, etc.; antihistaminic agents such as diphenhydramine hydrochloride, chlorpheniramine maleate, etc.; antibiotics such as talampicillin hydrochloride, etc.; antitumor antibiotics such as bleomycin hydrochloride, aclarubicin hydrochloride, vinblastine sulfate, etc.; vitamins such as thiamine nitrate, etc. These cationic pharmaceutically active substances may also be in the form of pharmaceutically acceptable salts thereof or free bases thereof.

In case that the pharmaceutically active substance is a peptide or a protein, the substance may be either anionic or cationic, depending upon pH of the composition. Accordingly, ionic compounds carrying counter charges can optionally be selected as required, taking into account a stable pH region for, e.g., a peptide or a protein. Examples of the peptide or protein include neocarzinostatin, zinostatin stilamer (SMANCS), interferon (e.g., α, β, γ), interleukin (e.g., IL-1 through IL-18), tumor necrosis factor (TNF), erythropoietin (EPO), granulocyte colony-stimulating factor (G-CSF), macrophage colony-stimulating factor (M-CSF), granulocyte macrophage colony-stimulating factor (GM-CSF), thrombopoietin (TPO), platlet-derived growth factor, stem cell growth factor (SCF), basic or acidic fibroblast growth factor (FGF) or a family thereof, nerve growth factor (NGF) or a family thereof, insulin-like growth factor (IGF), a super family of osteogenesis factor (e.g., BMP1 through BMP12) or transforming growth factor (TGFβ), hepatocyte growth factor (HGF), platelet-derived growth factor (PDGF), epidermal growth factor (EGF), insulin, calcitonin, glucagon, human growth hormone (hGH), parathyroid hormone (PTH), L-asparginase, superoxide dismutase (SOD), tissue plasminogen activator (t-PA) and the like. These peptides or proteins may be those having naturally occurring sequences or have altered sequences. Alternatively, the peptides or proteins may be modified (e.g., chemically modified with polyethylene glycol). The peptides or proteins may also be used as monomers or as homopolymers or heteropolymers.

The anionic pharmaceutically active substances or cationic pharmaceutically active substances are preferably synthetic ionic pharmaceutically active substances. While ionic prostanoic acid derivatives are excluded from the present invention, a certain compound out of the derivatives, e.g., (±)-(1R*,2R*,3aS*,8bS*)-2,3,3a,8b-tetrahydro-2-hydroxy-1-[(E)-(3S*)-3-hydroxy-4-methyl-1-octen-6-ynyl]-1H-cyclopenta[b]benzofuran-5-butanoic acid (generic name "beraprost") or salts thereof, which can be produced by the process described in Japanese Patent Application Laid-Open No. 58-124778, may be employed in some occasion for convenience to explain the effect of the present invention (the sodium salt of beraprost is commercially available as an anti-platelet agent or a blood flow improving agent under the generic name "beraprost sodium", which is also sometimes abbreviated simply as "BPS").

The amount of the ionic pharmaceutically active substance used in the present invention is not particularly limited, so long as it is within such an amount that generally exhibits a pharmacologically therapeutic effect. According to the present invention, even though the substance is sparingly soluble in water, the ionic pharmaceutically active substance can enjoy the benefits of sustained release by imparting hydrophobicity thereto, as in readily water-soluble substances.

The ionic compound having an opposite charge to that of the ionic pharmaceutically active substance increasing its hydrophobicity used in the present invention is not particularly restricted but preferably a substance containing a highly hydrophobic group(s). The presence of highly hydrophobic group(s) in the molecule of the ionic compound can increase the hydrophobic property of the ionic pharmaceutically active substance. The degree of hydrophobicity can be determined by calculating as an index the oil/water partition coefficient of the pharmaceutically active substance (that is, a ratio of, e.g., the concentration of the pharmaceutically active substance in an oil phase such as octanol to the concentration of the pharmaceutically active substance in water). Preferably, when the ionic compound is added to the pharmaceutically active substance in such an amount that the compound has a charge equivalent to that of the pharmaceutically active substance, the oil/water partition coefficient increases as compared to no addition of the compound. More preferably, when the compound having a counter ion is added to the pharmaceutically active substance in an excess amount to give more charges by, e.g., 20 times than equivalent one, the partition coefficient increases much more than the addition in an equivalent charge. The term "ionic" in the ionic compound of the present invention is used to mean that the compound contains one or more charged groups in the molecule thereof. The charged group functions as a hydrophilic group in the molecule. The ionic compound may additionally contain other hydrophilic groups not associated with charge. Preferably, the ionic compound contains one charged group in the molecule thereof Where the pharmaceutically active substance is anionic, the cationic compound to be incorporated preferably contains an ammonium, pyridinium, phosphonium or sulfonium group in the molecule thereof, or may be in the form of their salts. More preferably, the cationic compound contains the functional group mentioned above and the functional group carries a hydrophobic group having at least 6 carbon atoms. Examples of such cationic compounds are trialkylbenzyl ammonium salts such as benzyltriethylammonium chloride, benzyltributylammonium chloride, etc.; alkyldimethylbenzylammonium salts such as octyldimethylbenzylammonium chloride, lauryldimethylbenzylammonium chloride, myristyldimethylbenzylammonium chloride, stearyldimethylbenzylammonium chloride, benzalkonium chloride which is the mixture of lauryldimethylbenzylammonium chloride and myristyldimethylbenzylammonium chloride; benzethonium chloride or derivatives thereof; alkyltrimethyl salts such as lauryltrimethylammonium chloride, cetyltrimethylammonium chloride, lauryltrimethylammonium chloride, behenyltrimethylammonium chloride, etc.; alkyl pyridinium salts such as laurylpyridinium chloride, cetylpyridinium chloride, etc.; alkylamine salts such as oleylamine acetate, stearylamine acetate, etc.; alkylphosphonium salts such as tetrabutylphosphonium chloride, tricetyl(4-vinylbenzyl)phosphonium chloride, etc. or derivatives thereof. Examples of the cationic compounds include surface-active medicaments such as chlorpromazine hydrochloride, phenothiazine, perphenazine, perphenazine maleate, levomepromazine, lidocaine hydrochloride, meprylcaine hydrochloride, acetylcholine chloride, methylbenactyzium bromide, distigmine bromide, torazoline hydrochloride, imipramine hydrochloride, desipramine hydrochloride, amitriptyline hydrochloride, procaine hydrochloride, lidocaine hydrochloride, dibucaine hydrochloride, meprylcaine, diphenhydramine hydrochloride, chlorpheniramine maleate, iproheptine, etc. These cationic compounds may be in the form of pharmaceutically acceptable salts or free bases. Preferably, the salts are alkyldimethylbenzylammonium salts, alkyldimethylbenzylammonium salts, alkylpyridinium salts, alkylamine slats and alkylphosphonium salts, more preferably, alkyldimethylbenzylammonium salts, most preferably benzalkonium chlorides. These compounds may be used in combination of two or more.

In case that the pharmaceutically active substance is cationic, the anionic compound added as the ionic compound in the present invention contains preferably a carboxyl, sulfate, sulfonate or phosphate group in the molecule thereof. More preferably, the anionic compound contains the functional group(s) described above which carries a hydrophobic group of at least 6 carbon atoms. Examples of such anionic compounds include higher fatty acids such as caproic acid, caprylic acid, capric acid, lauric acid, myristic acid, palmitic acid, stearic acid, oleic acid, etc., or physiologically acceptable salts thereof (e.g., sodium or potassium); alkyl sulfates such as sodium lauryl sulfate, sodium myristyl sulfate, etc.; alkyl ether sulfates such as POE (2) lauryl ether sodium sulfate, etc.; alkylallyl sulfonates such as sodium lauryl sulfoacetate, etc.; alkyl sulfonates such as sodium dodecylbenzenesulfonate, etc.; sulfosuccinates; N-acylaminoacid salts such as sodium lauroylsarcosine, etc.; alkyl phosphates such as sodium laurylphosphate, etc.; alkyl ether phosphates or free acids thereof; bile acids or salts thereof such as sodium deoxycholate, etc.; and dialkylphosphatidinic acid salts such as sodium dipalmitoylphosphatidinate, etc. or free acids thereof. Preferably, the anionic compounds are sodium oleate and/or sodium laurylsulfate. These compounds may be used in combination of two or more.

The amount of the ionic compound to be added is not particularly limited so long as the compound is added in such an amount that can generally neutralize the charge of the pharmaceutically active substance and increase the hydrophobic property of the pharmaceutically active substance. The ionic compound is added preferably in the amount of 0.0001% to 50%, more preferably 0.001 to 10%, furthermore preferably 0.01 to 5%, all inclusive, in terms of weight/% by weight. The amount of the ionic compound to be added can be chosen to be the amount showing a desired sustained release pattern within the physiologically acceptable upper limit. The amount of the ionic compound added can be determined generally in terms of a molar ratio (charge ratio) based on the ionic pharmaceutically active substance and is preferably between 1 and 1,000, inclusive.

With respect to the pH of the sustained-release pharmaceutical composition of the present invention, its pH range is not particularly limited as far as pH is generally within a physiologically acceptable range but preferably it is in the range of 3 to 8. The pH can be suitably determined in view of stability of the ionic pharmaceutically active substance used in the invention.

The sustained-release pharmaceutical composition of the present invention can be prepared into a variety of pharmaceutical preparations in the form of, e.g., an aqueous solution, an oily preparation, a fatty emulsion, an emulsion, a gel, etc., and these preparations can be administered as intramuscular or subcutaneous injection or as injection to the organ, or as an embedded preparation or as a transmucosal preparation through nasal cavity, rectum, uterus, vagina, lung, etc. The composition of the present invention can also be administered in the form of oral preparations (e.g., solid preparations such as tablets, capsules, granules or powders; liquid preparations such as syrup, emulsions or suspensions). Inter alia, injecting is a preferred form of the preparations. Where the composition is prepared into an injection, the composition may contain, if necessary and desired, a known preservative, stabilizer, dispersing agent, pH controller or isotonic agent. Examples of the preservative are glycerin, propylene glycol, phenol, benzyl alcohol, etc. Examples of the stabilizer are dextran, gelatin, tocopherol acetate, alpha-thioglycerin, etc. Examples of the dispersing agent include polyoxyethylene (20) sorbitan monoolelate (Tween 80), sorbitan sesquioleate (Span 30), polyoxyethylene (160) polyoxypropylene (30) glycol (Pluronic F68), polyoxyethylene hydrogenated castor oil 60, etc. Examples of the pH controller include hydrochloric acid, sodium hydroxide, etc. Examples of the isotonic agent are glucose, D-sorbitol, D-mannitol, etc.

The sustained-release pharmaceutical composition of the present invention can be administered as an aqueous solution in its original composition since the composition itself exhibits the sustained release effect. In order to further increase the sustained release effect, however, the composition may be formulated with additional components such as vegetable oil, e.g., soybean oil, sesame oil, camellia oil, castor oil, peanut oil, rape seed oil, etc.; middle fatty acid triglycerides; fatty acid esters such as ethyl oleate; polysiloxane derivatives, etc.; alternatively, water-soluble high molecular weight compounds such as hyaluronic acid or salts thereof (weight average molecular weight: ca. 80,000 to 2,000,000), carboxymethylcellulose sodium (weight average molecular weight: ca. 20,000 to 400,000), hydroxypropylcellulose (viscosity in 2% aqueous solution: 3 to 4,000 cps), atherocollagen (weight average molecular weight: ca. 300,000), polyethylene glycol (weight average molecular weight: ca. 400 to 20,000), polyethylene oxide (weight average molecular weight: ca. 100,000 to 9,000,000), hydroxypropylmethylcellulose (viscosity in 1% aqueous solution: 4 to 100,000 cSt), methylcellulose (viscosity in 2% aqueous solution: 15 to 8,000 cSt), polyvinyl alcohol (viscosity: 2 to 100 cSt), polyvinylpyrrolidone (weight average molecular weight: 25,000 to 1,200,000), etc.

In the sustained-release pharmaceutical composition of the invention, it is preferred that the ionic pharmaceutically active substance be maintained in its dissolution state but may be in a suspension, since there is no particular limitation to the appearance.

A dose of the sustained-release pharmaceutical composition according to the present invention may be appropriately chosen, depending upon the amount of the composition or the pharmaceutically active substance contained in the composition, kind of diseases, age and body weight of the patient, frequency of administration, etc. In general, however, the dose is in the range of 0.1 $\mu$g to 10 g, preferably 10 $\mu$g to 1 g.

BEST MODE FOR CARRYING OUT THE INVENTION

Figure 1:
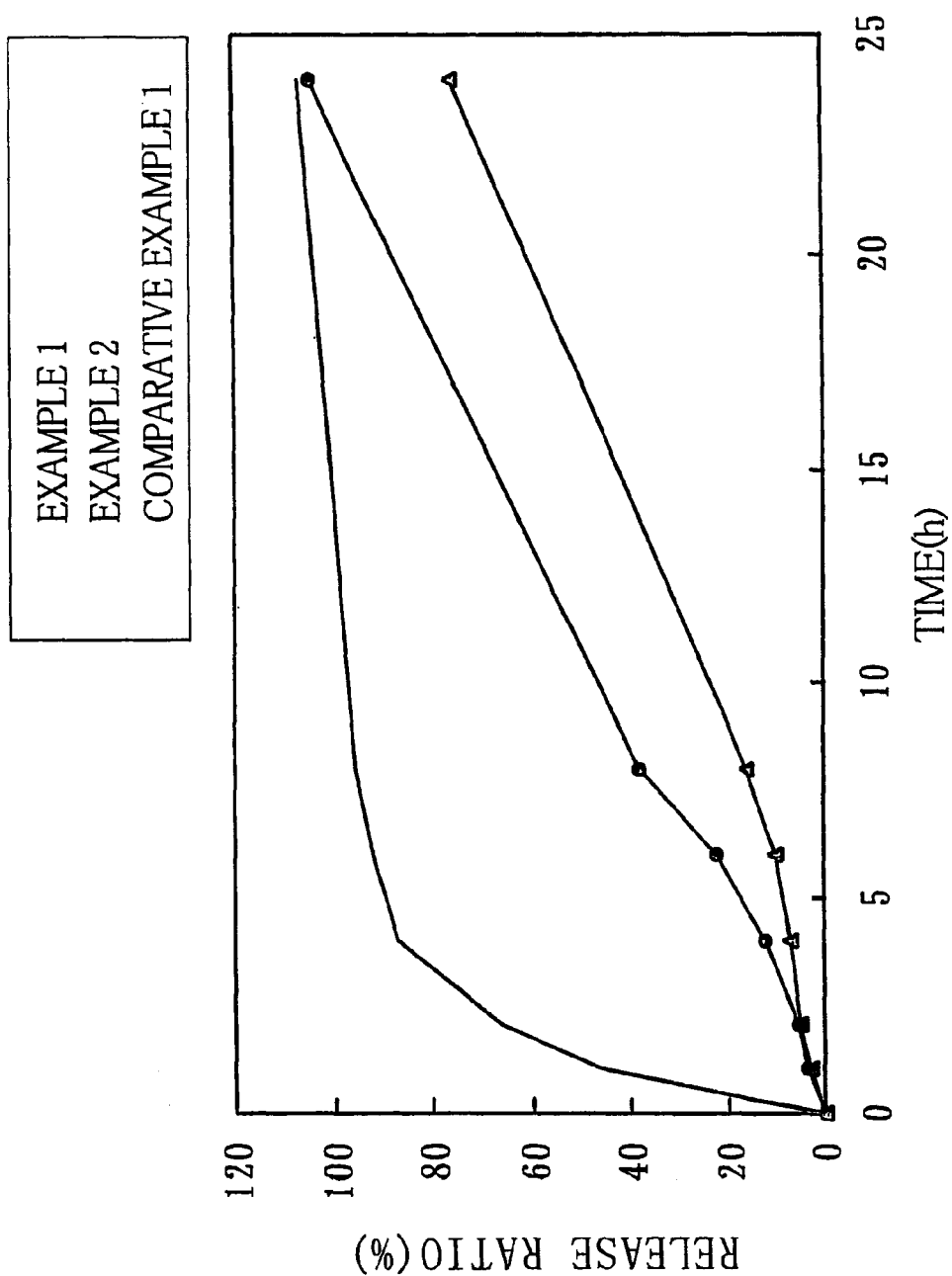
FIG. 1 shows a release behavior of diclofenac in Test 3 to determine the release of the preparations obtained in Examples 1 and 2 and Comparative Example 1, which test was carried out in 10 ml of a phosphate buffer solution (pH 7.4) at 37° C.

The present invention will be described below in more detail, with reference to Tests, Examples and Comparative Examples but is not deemed to be limited thereto.

REFERENCE TEST 1

Effect of the Ratio of Benzalkonium Chloride Added and pH on the Octanol/phosphate Buffer Partition Coefficient (PC) of BPS Method BPS was dissolved in phosphate buffer solution having pH of 5 to 8 in a concentration of 240 μg/ml. Various cations were added to the mixtures to give equivalent charge to that of BPS or 5 times or 20 times more than that of BPS. The same volume of octanol as that of the aqueous phase was added to the mixture followed by shaking at 37° C. for an hour. After centrifugation, the concentration of the pharmaceutically active substance in the aqueous phase was measured to calculate the partition coefficient.

> partition coefficient=concentration of the pharmaceutically active substance in the octanol phase/concentration of the pharmaceutically active substance in the aqueous phase Results and Discussion As a result, PC increased at pH of 7 as the amount of benzalkonium chloride added increased. This is considered to be because BPS with its hydrophobic degree being increased by the formation of ion complex is distributed in the octanol phase so that the equilibrium in the ion complex formation occured in the aqueous phase shifted toward the complex formation as the concentration of benzalkonium chloride became high. With respect to the pH, the partition coefficient of BPS, which is an acidic substance, decreased as the pH increased but the decrease in partition coefficient was suppressed by the addition of benzalkonium chloride. That is, the effect of benzalkonium chloride on the partition coefficient of BPS was greater in the high pH. When sodium chloride was added to make the solution isotonic, in which 20 times of equivalent molar ratio of benzalkonium chloride was included, the partition coefficient of BPS decreased. This is believed to be because the formation of ionic complex would be inhibited by the addition of sodium chloride. It was thus supported that the formation of ionic complex participated in the effect of enhancing the partition coefficient of BPS achieved by the addition of benzalkonium chloride.

TEST 1

Evaluation of Cationic Compound by Test in Terms of Partition Coefficient

A variety of cations were examined with their effect if these cations would affect the partition coefficient of diclofenac sodium (hereinafter sometimes simply referred to as "DIC") in octanol/phosphate buffer solution (pH 7).

Method

The pharmaceutically active substance was dissolved in an aqueous phase in a concentration of 240 μg/ml. Various cations were added to the solution to give equal charge to that of DIC or charges 20 times more than that of DIC. Then the same procedure as in Reference Test 1 was applied to calculate the partition coefficient.

Results and Discussion

With regard to the effect of various cations on the partition coefficient of the pharmaceutically active substance, representative results are shown in Table 1. An increase in the partition coefficient of he anionic pharmaceutically active substance was noted with alkylbenzylammonium salts such as triethylbenzylammonium chloride, etc., alkyltrimethylammonium salts such as lauryltrimetnylammonium chloride, etc.; phosphonium salts, lidocaine hydrochloride and meprylcaine hydrochloride. However, the partition coefficient of DIC showed no change with sorbitan sesquioleate (Span 30), which is a nonionic compound, and sodium lauryl sulfate, which is an anionic compound, for comparison, as compared to the partition coefficient when any ionic compound was not added (data not shown in Table 1); the results indicate that no effect was observed with the comparative compounds. Turning to the inorganic salts (magnesium chloride) or the compound having a small level of hydrophobicity (arginine hydrochloride), these compounds could form complexes but failed to enhance the hydrophobic property of DIC. Thus, no increase in the partition coefficient was noted. Furthermore, cationic hydroxyethylcellulose (Kachi-sero H-60, produced by Kao Corp., Japan) and protamine sulfate did not affect the partition coefficient; it is likely that these compounds contain hydrophilic groups represented by cationic groups so that overall the highly hydrophilic nature of molecules is presented with respect to the other hydrophobic groups present in the molecule and for this reason, the hydrophobic property of the pharmaceutically active substance would not be given enough even if complexes are formed.

TABLE 1

| Cation added | PC of BPS Equimolar Excess | | PC of DIC Equimolar Excess | |
|---|---|---|---|---|
| | amount | × 20 | amount | × 20 |
| Triethylbenzylammonium chloride | — | — | 14.0 | 25.7 |
| Tributylbenzylammonium chloride | 24.5 | 140 | 42.9 | 1030 |
| Octyldimethylbenzylammonium cloride | 60.9 | 568 | 75.5 | 6220 |
| Lauryldimethylbenzylammonium chloride | 71.2 | 1220 | 2780 | 12000 |
| Myristyldimethylbenzylammonium chloride | 64.5 | 1210 | 110 | 12300 |
| Stearyldimethylbenzylammonium chloride | 62.3 | 1350 | 1850 | 9640 |
| Benzethonium chloride | 70.8 | 1180 | 54.6 | 9320 |
| Lauryltrimethylammonium chloride | 83.5 | 985 | 596 | 11700 |
| Cetyltrimethylammonium chloride | 91.6 | 935 | 490 | 7690 |
| Stearyltrimethylammonium chloride | 83.4 | 995 | 1050 | 7190 |
| Behenyltrimethylammonium chloride | 59.5 | — | 1120 | — |
| Laurylpyridinium chloride | 75.0 | 1200 | 239 | — |
| Cetylpyridinium chloride | 77.8 | 1070 | 255 | 9060 |
| Oleylamine acetate | 30.4 | 473 | 62.2 | 3700 |
| Stearylamine acetate | 32.6 | 158 | 97.3 | 1020 |
| Lidocaine hydrochloride | 17.1 | 37.5 | 13.9 | 51.0 |
| Meprylcaine hydrochloride | 17.7 | 53.3 | 16.8 | 209 |
| Tetrabutylphosphonium chloride | — | — | 45.2 | 1190 |
| Tricetyl (4-vinylbenzyl)phoshphonium choride | — | — | 164 | 10300 |
| None | 16.2 | | 13.1 | |

That is, the results reveal that where the pharmaceutically active substance is anionic, the compounds having opposite charges such as quaternary ammonium or phosphonium groups and highly hydrophobic substituents (e.g., hydrophobic groups of 6 or more carbon atoms) exhibit the effect of increasing the hydrophobic property of the anionic pharmaceutically active substance.

REFERENCE TEST 2

Evaluation of Cationic Compound by Test in Terms of Partition Coefficient

A variety of cations were examined with their effect if these cations would affect the partition coefficient of BPS in octanol/phosphate buffer solution (pH 7).

Method as well as Results and discussion are the same as in Test 1. The results obtained are shown in Table 1 together with those of Test 1.

TEST 2

Evaluation of Anionic Compound by Test in Terms of Partition Coefficient

A variety of anions were examined with their effect if these anions would affect the partition coefficient of tamsulosin hydrochloride in octanol/phosphate buffer solution (pH 7).

Method

Tamsulosin hydrochloride was dissolved in an aqueous phase in a concentration of 100 µg/ml. Various anions were added to the mixtures to give equal charge to and charges larger by 5 times and 20 times than that of the medicament. Thereafter the same procedure was performed as in Reference Test 1 and the partition coefficient was calculated.

Results and Discussion

With regard to the effect of various anions on the partition coefficient of tamsulosin hydrochloride, representative results are shown in Table 2. The partition coefficient increased in the fatty acids or salts thereof (sodium salts in this test) in correlation to the addition amount (none, equimolar, x20). In particular, sodium lauryl sulfate, which is an alkyl sulfonate, showed the highest partition coefficient. However, Span 30 which is a nonionic compound, and benzalkonium chloride which is a cationic compound, used for comparison, showed the partition coefficient equivalent to or lower than the partition coefficient when no ionic compound was added (data not shown in Table 2). No increase in the partition coefficient was noted with tartaric acid, suberic acid, sebacic acid carboxymethylcellulose sodium (CMC-Na), sodium hyaluronate and Eudragit® L. This is believed because in these compounds the hydrophilic property is stronger in view of the balance between the hydrophilic and hydrophobic groups contained so that the hydrophobic property of the pharmaceutically active substance did not increase enough, even though the complex was formed.

TABLE 2

| Anion added | Partition coefficient of tamsulosin hydrochloride | |
| --- | --- | --- |
| | Equimolar amount | Excess (x20) |
| Sodium caproate | 4.21 | 4.93 |
| Sodium caprylate | 4.55 | 6.28 |
| Sodium caprate | 4.48 | 5.74 |
| Sodium laurate | — | 8.87 |

TABLE 2-continued

| Anion added | Partition coefficient of tamsulosin hydrochloride | |
| --- | --- | --- |
| | Equimolar amount | Excess (x20) |
| Sodium oleate | — | 5.38 |
| Sodium deoxycholate | 4.18 | 4.82 |
| Sodium lauryl sulfate | 5.93 | 85.0 |
| None | 3.87 | |

The above results reveal that where the pharmaceutically active substance is cationic, the compounds having opposite charges such as carboxyl or sulfate groups and highly hydrophobic substutients (e.g., hydrophobic groups of 6 or more carbon atoms) exhibit the effect of increasing the hydrophobic property of the cationic pharmaceutically active substance.

EXAMPLES 1 AND 2

Gel Preparation

After 0.1 part of DIC and 0.36 part of a cationic compound (benzalkonium chloride or cetyltrimethylammonium chloride) were dissolved in 89.54 parts of water, 10 parts of HPC-M was added to the solution. The mixture was stirred and fully swollen to give a gel preparation (Table 3).

TABLE 3

| Example | 1 | 2 |
| --- | --- | --- |
| DIC | 0.1 | 0.1 |
| Benzalkonium chloride | 0.36 | — |
| Cetyltrimethylammonium chloride | — | 0.36 |
| HPC-M | 10 | 10 |
| Water | 89.54 | 89.54 |

Comparative Example 1

A gel preparation for comparison was prepared in a manner similar to Example 1 except that no benzalkonium chloride was added.

EXAMPLES 3 THROUGH 7

Gel Preparation

After 0.1 part of DIC and benzalkonium chloride were dissolved in water, 5 parts of HPC-M was added to the solution. The mixture was stirred and fully swollen to give a gel preparation (Table 4).

TABLE 4

| Example | 3 | 4 | 5 | 6 | 7 |
| --- | --- | --- | --- | --- | --- |
| DIC | 0.1 | 0.1 | 0.1 | 0.1 | 0.1 |
| Benzalkonium chloride | 0.11 | 0.36 | 1.1 | 2.2 | 5.5 |
| HPC-M | 5 | 5 | 5 | 5 | 5 |
| Water | 94.79 | 94.54 | 93.8 | 92.7 | 89.4 |

EXAMPLES 8 THROUGH 11

Liquid Preparation

In water, 0.1 part of DIC and benzalkonium chloride were dissolved to give a liquid preparation (Table 5).

TABLE 5

| Example | 8 | 9 | 10 | 11 |
|---|---|---|---|---|
| DIC | 0.1 | 0.1 | 0.1 | 0.1 |
| Benzalkonium chloride | 0.11 | 0.36 | 1.1 | 2.2 |
| Water to make | 100 | 100 | 100 | 100 |

Comparative Example 2

A liquid preparation for comparison was prepared in a manner similar to Examples 8 through 11 except that no benzalkonium chloride was added.

EXAMPLES 12 THROUGH 15

Gel Preparation

After the anionic pharmaceutically active substance (sodium salicylate, calcium fenoprofen) and the cationic compound (benzalkonium chloride, cetyltrimethylammonium chloride) were dissolved in water, 10 parts of HPC-M was added to the solution. The mixture was stirred and fully swollen to give a gel preparation (Table 6).

TABLE 6

| Example | 12 | 13 | 14 | 15 |
|---|---|---|---|---|
| Sodium salicylate | 0.02 | 0.02 | — | — |
| Calcium fenoprofen | — | — | 0.02 | 0.02 |
| Benzalkonium chloride | 0.36 | — | 0.36 | — |
| Cetyltrimethylammonium chloride | — | 0.36 | — | 0.36 |
| HPC-M | 10 | 10 | 10 | 10 |
| Water | 89.62 | 89.62 | 89.62 | 89.62 |

EXAMPLES 16 THROUGH 18

Gel Preparation

After the anionic pharmaceutically active substance (sodium cefpiramid, minodronic acid) and the cationic compound (benzalkonium chloride, cetyltrimethylammonium chloride) were dissolved in water, 10 parts of HPC-M was added to the solution. The mixture was stirred and fully swollen to give a gel preparation (Table 7).

TABLE 7

| Example | 16 | 17 | 18 |
|---|---|---|---|
| Sodium cefpiramid | 0.02 | 0.02 | — |
| Minodronic acid | — | — | 0.02 |
| Benzalkonium chloride | 0.36 | — | 0.36 |
| Cetyltrimethylammonium chloride | — | 0.36 | — |
| HPC-M | 10 | 10 | 10 |
| Water | 89.62 | 89.62 | 89.62 |

EXAMPLES 19 THROUGH 22

Gel Preparation

After the cationic pharmaceutically active substance (tamsulosin hydrochloride, ramosetron hydrochloride) and the anionic compound (sodium oleate, sodium lauryl sulfate) were dissolved in water, 10 parts of HPC-M was added to the solution. The mixture was stirred and fully swollen to give a gel preparation (Table 8).

TABLE 8

| Example | 19 | 20 | 21 | 22 |
|---|---|---|---|---|
| Tamsulosin hydrochloride | 0.02 | 0.02 | — | — |
| Ramosetron hydrochloride | — | — | 0.02 | 0.02 |
| Sodium oleate | 0.36 | — | 0.36 | — |
| Sodium lauryl sulfate | — | 0.36 | — | 0.36 |
| HPC-M | 10 | 10 | 10 | 10 |
| Water | 89.62 | 89.62 | 89.62 | 89.62 |

Comparative Example 3

A gel preparation for comparison was prepared in a manner similar to Examples 19 and 20 except that no sodium oleate or sodium lauryl sulfate was added.

TEST 3

Effect of Release Test In Vitro

Each of the gel preparations obtained in Examples 1 and 2, Comparative Example 1 and Examples 12, 13, 14, 15,16, 17 and 18 was assessed, respectively, with regard to the release of the active substance in 10 ml of a phosphate buffer solution (pH 7.4) at 37° C.

The results of the release test are shown in FIG. 1. According to the results, a delayed release was confirmed with the quaternary ammonium salt with the hydrophobic property being enhanced in the partition coefficient test, while no delayed release was noted in some of Comparative Examples.

TEST 4

In Vivo Effect in Rat(Effect of the Amount of Cations Added)

The gel preparations of Examples 3 to 7, the liquid preparations of Examples 8 to 11 and Comparative Example 2 were subcutaneously given to Wistar strain male rats (age of 8 weeks) at the back, respectively, to determine the concentration of the active substance in plasma with passage of time.

Figure 2:
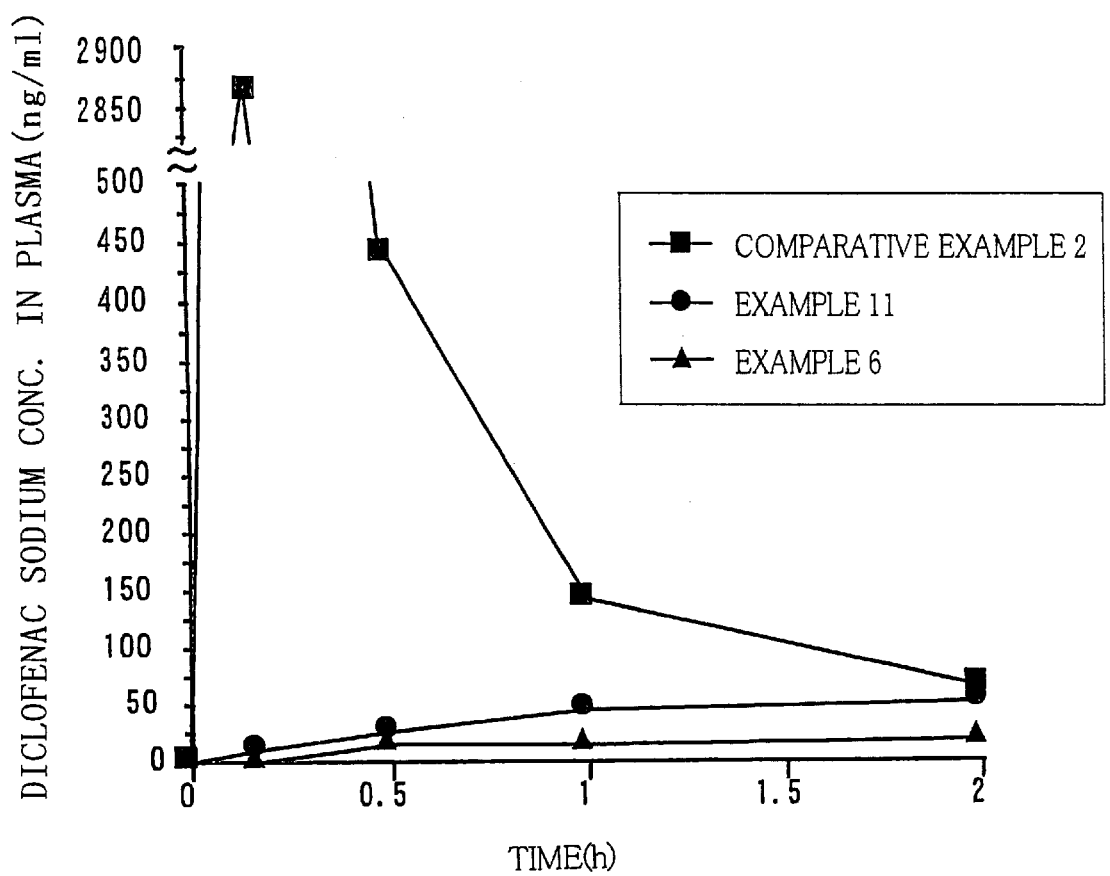
FIG. 2 shows the concentration of medicaments in plasma plotted with passage of time in Test 4, when the preparations obtained in Examples 6, 11 and Comparative Example 2 were subcutaneously given to Wistar strain male rats (age of 8 weeks) at the back.

The results are shown in FIG. 2 in terms of the plasma concentration with passage of time. According to the results, the change in plasma concentration of the active substance shows a sustained release pattern with correlation to the amount of benzalkonium chloride added, suggesting that the sustained release pattern can be controlled by changing the addition amount. On the contrary, no sustained release was noted with some of Comparative Examples.

TEST 5

Effect of Release Test In Vitro

Each of the gel preparations obtained in Examples 19 and 20, Comparative Example 3 and Examples 21 and 22 was assessed, respectively, with regard to the release of the active substance in 10 ml of a phosphate buffer solution (pH 7.4) at 37° C.

According to the results, a delayed release was confirmed with the alkyl organic acid salts which were shown to have enhanced hydrophobic property in the partition coefficient test, while no delayed release was noted in some of Comparative Example.

REFERENCE EXAMPLE 1

Gel Preparation

After 0.024 part by weight (hereinafter merely referred to as "part") of BPS and 0.29 part of capryldimethylbenzylammonium chloride (which molar amount was adjusted to correspond to 0.36 part of benzalkonium chloride) were dissolved in 89.686 parts of water, 10 parts of hydroxypropylcellulose (trademark: HPC-M) was added to the solution. The mixture was stirred and fully swollen to give a gel preparation.

REFERENCE EXAMPLES 2 THROUGH 9

Gel Preparation

Gel preparations having the same parts as in Reference Example 1 were prepared in a manner similar to Reference Example 1 except that capryldimethylbenzylammonium chloride of Reference Example 1 was replaced by other cationic compounds shown in Table 9.

TABLE 9

| Reference Example | Cationic compound |
| --- | --- |
| 2 | Lauryldimethylbenzylammonium chloride |
| 3 | Myristyldimethylbenzylammonium chloride |
| 4 | Stearyldimethylbenzylammonium chloride |
| 5 | Lauryltrimethylammonium chloride |
| 6 | Cetyltrimethylammonium chloride |
| 7 | Stearyltrimethylammonium chloride |
| 8 | Behenyltrimethylammonium chloride |
| 9 | Benzethonium chloride |

Comparative Reference Examples 1 Through 3

After 0.024 part of BPS was dissolved in water, 10 parts of HPC-M was added to the solution. The mixture was stirred and fully swollen to give a gel preparation.

Furthermore, arginine hydrochloride and magnesium sulfate were added to the above preparation, respectively to give gel preparations. These preparations were used as comparative reference samples (Table 10).

TABLE 10

| Comparative Reference | 1 | 2 | 3 |
| --- | --- | --- | --- |
| BPS | 0.024 | 0.024 | 0.024 |
| Arginine hydrochloride | — | 0.1 | — |
| Magnesium sulfate 7H$_2$O | — | — | 0.1 |
| HPC-M | 10 | 10 | 10 |
| Water | 89.976 | 89.876 | 89.876 |

REFERENCE TEST 3

In Vitro Release Test of Gel Preparation Using Various Cations

Each of the gel preparations obtained in Reference Examples 1 to 9 and Comparative Reference Examples 1 to 3 was evaluated, respectively, with regard to the release of the active substance in 10 ml of a phosphate buffer solution (pH 7.4) at 37° C.

According to the results, a delayed release was confirmed with the quaternary ammonium salt that was shown to enhance the hydrophobic property in the partition coefficient test (Reference Test 2). On the other hand, no delayed release was noted with magnesium sulfate and arginine hydrochloride in the reference test, which are divalent inorganic metal salts similar to magnesium chloride demonstrated to hardly enhance the partition coefficient. These results thus suggest that there is a correlation between the effect of enhancing the partition coefficient and the sustained release effect.

REFERENCE EXAMPLE 10

Gel Preparation

After 0.024 part of BPS and 0.02 part of benzalkonium chloride were dissolved in 89.956 parts of water, 10 parts of HPC-M was added to the solution. The mixture was stirred and fully swollen to give a gel preparation.

REFERENCE EXAMPLES 11 THROUGH 17

Gel Preparation

Gel preparations having the amounts of BPS, benzalkonium chloride, HPC-M and water shown in Table 11 were prepared in a manner similar to Reference Example 10.

Comparative Reference Example 4

A gel preparation for comparison was prepared in a manner similar to Reference Example 17 except that no benzalkonium chloride was added.

TABLE 11

| | Reference Example | | | | | | |
| --- | --- | --- | --- | --- | --- | --- | --- |
| | 11 | 12 | 13 | 14 | 15 | 16 | 17 |
| BPS | 0.024 | 0.024 | 0.024 | 0.002 | 0.002 | 0.002 | 0.002 |
| Benzalkonium chloride | 0.1 | 0.2 | 0.36 | 0.002 | 0.1 | 0.2 | 0.36 |
| HPC-M | 10 | 10 | 10 | 5 | 5 | 5 | 5 |
| Water | 89.876 | 89.776 | 89.616 | 94.996 | 94.898 | 94.798 | 94.638 |

REFERENCE TEST 4

Effect of the Amount of Counter Ions Added on Release in Gel Preparation

Release test was carried out in 10 ml of a phosphate buffer solution (pH 7.4) at 37° C., using the preparations obtained in Reference Examples 11 Through 13 and Comparative Reference Example 1.

The results reveal that release of BPS from the preparation of the present invention was apparently controlled as compared to the Comparative Reference Example and the release was delayed in correlation to the addition amount of benzalkonium chloride, which is a counter ion.

REFERENCE TEST 5

Effect of the Addition Amount of Benzalkonium Chloride in Rat In Vivo

The gel preparations obtained in Reference Example 17 and Comparative Reference Example 4 were subcutaneously given to Wistar strain male rats (age of 8 weeks) at the back, respectively. The concentration of the active substance in plasma was determined with passage of time.

In the preparation of the present invention (added with benzalkonium chloride), the change in plasma concentration of the active substance showed a sustained release as compared to the comparative example. It is considered also from the foregoing results in vitro (Reference Test 4) that the sustained release pattern can be controlled by changing the amount of benzalkonium chloride added.

REFERENCE EXAMPLE 18
Liquid Preparation

In 99.638 parts of water, 0.002 part of BPS and 0.36 part of benzalkonium chloride were dissolved to give a liquid preparation.

Comparative Reference Example 5
Liquid Preparation

A liquid preparation for comparison was prepared in a manner similar to Reference Example 18 except that no benzalkonium chloride was added.

REFERENCE EXAMPLE 19
Emulsion Preparation

After 0.002 part of BPS and 0.36 part of benzalkonium chloride were dissolved in 94.638 parts of water, 5 parts of soybean oil was added to the solution. An emulsion preparation was prepared using a microfluidizer (12,000 psi, 10 minutes at room temperature).

REFERENCE EXAMPLES 20 THROUGH 24
Emulsion Preparation

Emulsion preparations having the amounts of BPS, benzalkonium chloride, other additives (surfactant, oil, etc.) and water shown in Table 12 were prepared in a manner similar to Reference Example 19.

TABLE 12

| | Reference Example | | | | |
|---|---|---|---|---|---|
| | 20 | 21 | 22 | 23 | 24 |
| BPS | 0.002 | 0.002 | 0.002 | 0.002 | 0.002 |
| Benzalkonium chloride | 0.36 | 0.36 | 0.36 | 0.36 | 0.36 |
| Pluronic F68 | 1.8 | — | — | 1.8 | — |
| Tween 80 | — | 1.8 | — | — | 1.8 |
| Soybean oil | 10 | 10 | — | — | — |
| Sesame oil | — | — | 5 | 10 | 10 |
| Concentrated glycerin | 2.21 | 2.21 | — | 2.21 | 2.21 |
| Water to make | 100 | 100 | 100 | 100 | 100 |

REFERENCE EXAMPLE 25

After 0.002 part of BPS and 0.36 part of benzalkonium chloride were dissolved in 2 parts of ethanol, soybean oil was added to the solution to make the volume 100 parts. Thus, an oily preparation was prepared.

REFERENCE EXAMPLES 26 THROUGH 30
Oily Preparation

After BPS and benzalkonium chloride were dissolved in alcohols (ethanol, benzyl alcohol, benzyl benzoate), oil (soybean oil, sesame oil) was added to the solution, all in the amount indicated in Table 13, to make the volume 100 parts. Thus, oily preparations were prepared.

TABLE 13

| | Reference Example | | | | |
|---|---|---|---|---|---|
| | 26 | 27 | 28 | 29 | 30 |
| BPS | 0.002 | 0.002 | 0.002 | 0.002 | 0.002 |
| Benzalkonium chloride | 0.36 | 0.36 | 0.36 | 0.36 | 0.36 |

TABLE 13-continued

| | Reference Example | | | | |
|---|---|---|---|---|---|
| | 26 | 27 | 28 | 29 | 30 |
| Ethanol | — | — | 2 | — | — |
| Benzyl alcohol | 2 | 5 | — | 2 | 5 |
| Benzylbenzoate | 20 | — | — | 20 | — |
| Soybean oil to make | 100 | 100 | — | — | — |
| Sesame oil to make | — | — | 100 | 100 | 100 |

REFERENCE EXAMPLES 31 THROUGH 34
Gel Preparation

After 0.002 part of BPS and 0.36 part of benzalkonium chloride were dissolved in water, a gel base (CMC-Na, sodium hyaluronate, atherocollagen, gelatin) was added to the solution. The mixture was stirred and fully swollen to give gel preparations Cable 14).

TABLE 14

| Reference Example | 31 | 32 | 33 | 34 |
|---|---|---|---|---|
| BPS | 0.002 | 0.002 | 0.002 | 0.002 |
| Benzalkonium chloride | 0.36 | 0.36 | 0.36 | 0.36 |
| CMC-Na | 3 | — | — | — |
| Na hyaluronate | — | 2.5 | — | — |
| Atherocollagen | — | — | 2 | — |
| Gelatin | — | — | — | 10 |
| Water | 96.638 | 97.138 | 97.638 | 89.638 |

REFERENCE EXAMPLES 35 THROUGH 38
Cream Preparation

After 0.002 part of BPS and 0.36 part of benzalkonium chloride were dissolved in water, a gel base (HPC-M, CMC-Na, sodium hyaluronate, atherocollagen) was added to the solution. The mixture was stirred to give cream preparations (Table 15).

TABLE 15

| Reference Example | 35 | 36 | 37 | 38 |
|---|---|---|---|---|
| BPS | 0.002 | 0.002 | 0.002 | 0.002 |
| Benzalkonium chloride | 0.36 | 0.36 | 0.36 | 0.36 |
| HPC-M | 5 | — | — | — |
| CMC-Na | — | 3 | — | — |
| Na hyaluronate | — | — | 2.5 | — |
| Atherocollagen | — | — | — | 2 |
| Water | 74.638 | 76.638 | 77.138 | 77.638 |
| Soybean oil | 20 | 20 | 20 | 20 |

REFERENCE TEST 6
In Vivo Effect in Rat

Each of the liquid preparations obtained in Reference Example 18 and Comparative Reference Example 5, the emulsion preparations of Reference Examples 19 to 21, the oily preparations obtained in Reference Examples 25 to 28 and the gel preparations or cream preparations obtained in Reference Examples 31 to 38 was subcutaneously given to Wistar strain male rats (age of 8 weeks) at the back to determine the concentration of the active substance in plasma with passage of time.

The results reveal that the sustained release effect was obtained with the respective preparations, by adding counter ions. To the contrary, no sustained release effect was noted with some of the Comparative Reference Examples.

INDUSTRIAL APPLICABILITY

The present invention is useful as providing the sustained-release pharmaceutical composition which exhibits excellent sustained release effect of the ionic pharmaceutically active substance (excluding ionic prostanoic acid derivatives), irrespective of water solubility possessed by the ionic pharmaceutically active substance. The sustained release according to the present invention is effected by means of a technique quite different from conventional techniques including those adopted to sustain the release of ionic pharmaceutically active substances, to insolubilize a pharmaceutically active substance itself and to retard dissolution of such a substance by microencapsulation. The present invention is also useful in that the sustained release can be achieved by the invention to a fully satisfactory extent that was not obtained by known techniques.

The pharmaceutical composition of the present invention can attain excellent sustained release effect not only in the form of injection but also in all other pharmaceutical preparations including implants, transmucosal and oral preparations.

What is claimed is:

1. A sustained-release pharmaceutical composition for an ionic pharmaceutically active substance comprising an ionic pharmaceutically active substance (excluding an ionic prostanoic acid derivative) and an ionic compound having an opposite charge to that of the ionic pharmaceutically active substance and increasing hydrophobicity of the active substance, wherein the ionic compound is incorporated at least in an equimolar amount based on the pharmaceutically active substance in terms of a charge ratio.

2. A sustained-release pharmaceutical composition according to claim 1, wherein the ionic compound having an opposite charge to the ionic pharmaceutically active substance and increasing the hydrophobic property of the active substance contains a hydrophobic group in the molecule thereof.

3. A sustained-release pharmaceutical composition according to claim 1, wherein the ionic compound increases an oil/water partition coefficient of the ionic pharmaceutically active substance.

4. A sustained-release pharmaceutical composition according to claim 1, wherein the ionic pharmaceutically active substance is anionic.

5. A sustained-release pharmaceutical composition according to claim 4, wherein the ionic compound is a compound containing a group selected from an ammonium, pyridinium, phosphonium and sulfonium group in the molecule thereof, or a salt thereof.

6. A sustained-release pharmaceutical composition according to claim 5, wherein the ionic compound contains at least one member selected from the group consisting of an alkyldimethylbenzylammonium salt, an alkyltrimethylammonium salt, an alkylpyridinium salt, an alkylamine salt and an alkylphosphonium salt.

7. A sustained-release pharmaceutical composition according to claim 1, wherein the ionic compound is benzalkonium chloride.

8. A sustained-release pharmaceutical composition according to claim 4, wherein the ionic pharmaceutically active substance is a synthetic ionic pharmaceutically active substance.

9. A sustained-release pharmaceutical composition according to claim 1, wherein the ionic pharmaceutically active substance is cationic.

10. A sustained-release pharmaceutical composition according to claim 9, wherein the ionic compound is a compound containing a group selected from a carboxyl, sulfate, sulfonate and phosphate groups in the molecule thereof, or a salt thereof.

11. A sustained-release pharmaceutical composition according to claim 10, wherein the ionic compound is sodium lauryl sulfate and/or sodium oleate.

12. A sustained-release pharmaceutical composition according to claim 9, wherein the ionic pharmaceutically active substance is a synthetic ionic pharmaceutically active substance.

* * * * *